United States Patent [19]
Musick et al.

[11] Patent Number: 5,990,288
[45] Date of Patent: Nov. 23, 1999

[54] METHOD FOR PURIFYING FSH

[75] Inventors: James R. Musick, Conifer; Erik Van Horn, Englewood, both of Colo.

[73] Assignee: Vitro Diagnostics, Inc., Littleton, Colo.

[21] Appl. No.: 09/075,423

[22] Filed: May 8, 1998

Related U.S. Application Data

[60] Provisional application No. 60/065,405, Oct. 21, 1997, abandoned.

[51] Int. Cl.$^6$ .............................. C07K 3/18; C07K 3/20; C07K 3/28
[52] U.S. Cl. .......................... 530/398; 530/397; 530/350; 530/412; 530/413; 530/415; 530/344
[58] Field of Search ................................... 530/344, 397, 530/398, 350, 412, 413, 415

[56] References Cited

U.S. PATENT DOCUMENTS

| | | |
|---|---|---|
| 4,487,833 | 12/1984 | Donahoe . |
| 4,734,398 | 3/1988 | diZerega . |
| 4,764,502 | 8/1988 | diZerega ..................... 514/2 |
| 5,128,453 | 7/1992 | Arpaia et al. ........................... 530/398 |
| 5,173,404 | 12/1992 | diZerega .................. 435/7.1 |
| 5,661,126 | 8/1997 | Donahoe . |

FOREIGN PATENT DOCUMENTS 2173803A   10/1986   United Kingdom .

OTHER PUBLICATIONS

Declaration of James R. Musick and Erik Van Horn.
International Search Report.
Jack, G.W., "Immunoaffinity Chromatography," Mol. Biotechnology, 1,, pp. 59–86 (1994).
Lowe, C.R. et al,, "Designer dyes: 'biomimetic' ligands for the purification of pharmaceutical proteins by affinity chromatography," Tibtech, 10, pp. 442–448 (1992).
Moore, L.G., et al, "Follicle–Stimulating Hormone in the Brushtail Possum (*Trichosurus vulpecula*): Purification, Characterization, and Radioimmunoassay," Gen. Comp. Endo., 106, pp. 30–38 (1997).

*Primary Examiner*—F. T. Moezie
*Attorney, Agent, or Firm*—McCutchen, Doyle, Brown & Enersen, LLP

[57] ABSTRACT

The present invention provides a method for purifying follicle stimulating hormone (FSH) from biological samples, for example, from human pituitary glands or human postmenopausal urine, wherein the FSH is contaminated with other proteins, by use of dye-ligand affinity chromatography (DAC). This process may be used to generate affinity pure FSH suitable for therapeutic applications.

16 Claims, No Drawings

METHOD FOR PURIFYING FSH

Applicants claim priority under 35 U.S.C. Section 119(e) of U.S. Provisional Application, Ser. No. 60/065,405 filed Oct. 21, 1997 now abandoned.

TECHNICAL FIELD

The present invention relates to follicle stimulating hormone, follitropin, ("FSH") and to a process for producing highly purified FSH.

BACKGROUND OF THE INVENTION

FSH is a pituitary heterodimeric glycoprotein hormone synthesized and released from gonadotrope cells of the anterior pituitary gland. As a circulating hormone, FSH interacts with high affinity with receptor molecules on the surface of granulosa cells in the ovary. This interaction evokes a series of intracellular events, including a cyclic AMP second message and elicitation of a steroidogenic response by the granulosa cells resulting in estrogen production. Local estrogen and FSH stimulation promote the growth and maturation of ovarian follicles.

The amount of circulating FSH is dependent upon several other endocrine and neural factors. Gonadotropin releasing hormone (GnRH) is a peptide elaborated by neurons of hypothalamus. Released GnRH interacts with receptors on pituitary gonadotrope cells to control the synthesis and release of FSH and LH from the anterior pituitary gland. FSH secretion is also effected by circulating levels of steroid hormones. The steroidogenic response of granulosa cells to FSH results in gradually increasing estradiol levels. When serum estradiol reaches a critical level, it triggers a large increase in the rate of LH and FSH release from the anterior pituitary. The resultant LH surge induces ovulation and luteinization of granulosa cells. Progesterone is released from the corpus luteum following ovulation and this steroid prepares the uterus for implantation of the fertilized ovum. Elevated levels of estrogens and progesterone exert a negative feedback inhibition at hypothalamic sites to lower FSH and LH synthesis and release. Hence, the effects of steroids on gonadotropin release depend on the circulating levels; at low levels of estrogen, FSH and LH are positively regulated while higher levels result in negative feedback inhibition.

In males, FSH induces spermatogenesis through a proliferative effect on spermatocytes. Sperm production also requires testosterone, which is under positive regulatory control by LH.

An apparent paradox of the above-described hormonal control process is the production of both LH and FSH by the gonadotrope cell while GnRH serves as a positive regulatory agent for both hormones. Work within the last 10 years suggests that the peptides, activin, follistatin and inhibin selectively regulate FSH secretion from the anterior pituitary gland. FSH synthesis and release is activated by activin while inhibin and follistatin have negative feedback effects. The inhibitory effect of follistatin is thought to be mediated by its high-affinity binding to activin and blockage of its biological activity. There is evidence for both autocrine and paracrine local regulatory effects of these peptides and for feedback effects of inhibin released from gonadal tissue. Both inhibin and activin are structurally related and are members of the diverse transforming growth factor beta family of peptides. Study of the physiological roles of activin, follistatin and inhibin is a current area of active research (Reviewed by Knight, 1996).

FSH has been used extensively as a drug to treat human infertility by induction of follicular development in females. Earlier products were crude preparations of LH and FSH, i.e., Pergonal®. Products that are more recent have been purer FSH preparations. Metrodin®, has low levels of LH and the FSH specific activity is about 100 IU/Mg. This drug requires intramuscular injections every day for 5 to 7 days, followed by a single injection of hCG to induce ovulation. A recent advance is Fertinex® which is affinity pure FSH, purified from hMG. This product exhibits a potency of 8500 to 13,500 IU/Mg at 95% purity. The high purity of Fertinex® allows delivery by subcutaneous injection, which can be administered at home. Following administration of Fertinex®, hCG is used for induction of ovulation. Depending on the dosage of FSH administered, it may be used to promote in vivo fertility or, at higher dosages, it may be used to induce multiple oocyte formation for in vitro fertilization procedures. Recombinant forms of FSH (Puregon® and Gonal®) also are used as fertility drugs.

FSH has been purified from pituitary glands, human postmenopausal urine and from culture media collected from genetically engineered cells. FSH purification has been an active area of research over the past 30 years. Older methods rely on procedures such as ion exchange chromatography, size exclusion chromatography, polyacrylamide gel electrophoresis and chromatography on hydroxylapatite. In the method of Roos (1968) a FSH preparation of 14,000 IUs biological activity/Mg was obtained from fresh frozen human pituitary glands with an overall recovery of activity of 5.0%. A similar procedure applied to urinary FSH resulted in a preparation of 780 IU/Mg at a 7.7% overall yield. Because of the similar physicochemical properties of FSH and LH, i.e., similar molecular weight and overlapping isoelectric profiles, affinity chromatography methods have been employed to improve the separation of LH and FSH. In addition, affinity methods afford the possibility of high purification in a single step (up to 100-fold) thereby reducing the number of steps in a purification method and improving overall yield. The latter is a critical factor in the commercial production of FSH as overall yield is a major determinant of cost. Group specific affinity adsorbents such as the lectin Concanavalin A or chitosan (Japanese patent number 8,027,181) bind glycoproteins via specific carbohydrate groups. While these ligands are ineffective in the separation of two glycoproteins such as FSH and LH, Concanavalin A has been used to characterize microheterogeneity of purified FSH preparations (e.g., Chappel, et.al., 1983).

Immunoaffinity chromatography (IAC) relies upon the specificity of mono- or polyclonal antibodies for capture of specific protein antigens from crude mixtures. Antibodies may first be screened for use in IAC (Bonde, et.al., 1991). The selected antibodies are coupled to a chromatographic solid phase, e.g., cross-linked agarose, through covalent bonds, e.g., cyanogen bromide (CNBr) or other coupling chemistries targeting surface amino, hydroxyl, carboxyl or sulfhydryl groups of immunoglobulins to form a solid matrix. Recent coupling methods attempt site-directed immobilization of antibodies in an effort to optimize antigen-binding efficiencies, which are typically low, using classical coupling chemistries. One method of site-directed coupling is through carbohydrate groups of the $F_c$ immunoglobulin region to hydrazide-activated solid supports (e.g., Hoffman and O'Shannessy (1988)). The solid phase coupled to antibody is then packed in a chromatography column and equilibrated with buffer for binding to antigen. Mixtures of target protein and contaminants are equilibrated with binding buffer and then applied to the column. Non-adsorbed contaminants are removed by washout with various buffers. Elution occurs by use of chaotropic agents, extremes of pH, changes in ionic strength, etc. Elution is a critical aspect of IAC since the elution conditions may alter the biological activity of the immobilized antibody or the eluted antigen or both (reviewed by Jack, 1994).

IAC may be used to remove specific contaminants from a crude mixture. This mode was first applied to FSH purification using antibodies to hCG, which through cross reactivity to LH, effectively reduced LH contamination levels (Donini, et.al., 1966). Jack, et.al., (1987) and Great Britain patent number 8,510,177, utilized monoclonal antibody specific to FSH for IAC. The antibody was coupled to CNBr-activated Sepharose 4B. Samples were applied in 0.05M borate buffer, 0.5 M NaCl at pH 8.5 and non-adsorbed contaminants were eluted from the column with 0.05 M borate at pH 8.5. The bound FSH was eluted using 0.1M glycine, 0.5 M NaCl at pH 3.5. When using a sample containing the glycoprotein-enriched fraction from a side-fraction of human growth hormone obtained from frozen pituitaries, 47% of the applied FSH was recovered from the IAC procedure. The FSH was recovered at a specific immunological activity of 10,000 IU/mg (Biological specific activity=1.2× immunological). It contained 0.0014 IU LH per IU FSH and 0.93 $\mu$IUs TSH/IU FSH (Jack, et.al., 1987). Another IAC method for FSH is described in U.S. Pat. No. 5,128,453. This method relies on a monoclonal antibody to FSH that is coupled to Sepharose 4B by divinylsulphone. The column and sample was equilibrated with 0.1M Tris, 0.3 M NaCl at pH 7.5 and the IAC procedure was performed at 4° C. In this case, partially purified urinary FSH (hMG) was used as a sample. The sample was applied in the equilibration buffer and nonadsorbed materials were removed by continued elution with this buffer. Elution was accomplished by use of alkaline buffers, e.g., 1M ammonia and other eluent of pH>11 and of ionic molarity higher than 0.8 M. The product of IAC was then subject to reverse phase HPLC on a C18 column to generate the final product. While the yield of FSH activity from the IAC step was not given, the final product had a specific biological activity of 6200 IU/Mg and had undetectable levels of LH contamination by RIA measurement. No other protein contaminants were detected by SDS-PAGE analysis. Other researchers have recently reported the use of dye affinity chromatography (DAC) in the purification of FSH from the bushtail possum. Their purification involved several steps including the use of Green A Matrix gel and Red A Matrix gel (Amicon, Inc.) for two sequential DAC procedures. The overall yield of their method was 12% (Moore, et.al., 1997).

SUMMARY OF THE INVENTION

The present invention provides a process for the purification of FSH by use of DAC. The method utilizes a dye ligand, for example an orange dye ligand, preferably Orange 1 (Affinity Chromatography Ltd.), which is coupled to cross-linked agarose via triazine coupling chemistry to form a solid matrix. Other solid matrices could also be used comprising a dye, for example, yellow 2 and green 1. Orange 1 shows strong selectivity to FSH when the binding occurs at low ionic strength at acidic pH, for example, about pH 4.0. Samples containing FSH and excess amounts of LH fail to exhibit significant LH binding under these conditions and LH contamination is conveniently removed by elution with an appropriate washout buffer. FSH may then be eluted from the dye by a linear salt gradient, preferably 0 to 0.6 M NaCl, or other means of increasing eluent conductivity. Other means of eluting or releasing the bound FSH may be used such as, for example, agents which compete for FSH binding to the dye ligand. The result is a FSH product containing only minimal contamination by LH and other unwanted proteins. Residual contamination of FSH by LH and other unwanted proteins may then be removed by, for example, hydrophobic interaction chromatography (HIC) or ion exchange chromatography. The FSH purification method of the present invention has been used to purify, for example, human pituitary FSH and human urinary FSH.

The present method also may be used to purify FSH from other species, particularly mammalian, including, for example, bovine, equine, porcine, ovine, canine, feline, rat, mouse and monkey. The present invention operates at high yields (>95% recovery of FSH activity) and with high purification factors (up to about 50-fold) depending upon the sample used. The method is non-denaturing to FSH and this allows for high overall recoveries in multi-step purification procedures as needed, for example, when FSH is purified from human pituitary glands. Also, the ligand shows minimal ligand leakage and can be regenerated with complete restoration of FSH binding properties. Therefore, the dye may be used for at least 25 cycles prior to loss of effective binding and release of FSH.

The advances of this invention over the prior art include the advantages of affinity chromatography by DAC as compared to IAC. The primary advance is in the ease of elution of bound FSH from the immobilized dye ligand as compared to an immobilized antibody. While very gentle elution conditions are used in the present invention, e.g., sodium chloride gradient at pH 6.0, elution from an IAC column usually involves relatively harsh conditions. The method of Jack, et.al.,(1987) involves use of pH 3.5 to elute bound FSH. This pH has deleterious effects on the immunological activity of human FSH. While use of alkaline pH, as in the method of U.S. Pat. No. 5,128,453, eliminates the harmful effects of low pH, the effects of this pH on the immobilized antibody are unknown. Even minor effects on the immobilized antibody could tend to decrease the effectiveness of the immunoadsorbant with continued use cycles. In addition, IAC requires highly consistent batches of monoclonal antibody and coupling procedures, which may result in low antigen binding efficiencies. Lower binding capacity would require larger amounts of antibody to bind a given amount of antigen. DAC relies on an inert ligand, which can be manufactured and coupled in a highly reproducible manner.

Another advantage of DAC resins is in sanitation. DAC resins may by sanitized and depyrogenated by treatment with 1.0 N NaOH without effect on chromatographic performance. Such treatment of IAC resins would usually result in inactivation of the antibody. Therefore, sanitation of IAC resins is more difficult to achieve. Minimal ligand leakage from DAC resins also results in lower product contamination, while antibody leakage from IAC resins can contaminate the product. For reviews of DAC see: Lowe, et.al., (1992) and Garg, et.al., (1996).

DETAILED DESCRIPTION OF THE INVENTION

This invention is intended for use with biological materials, particularly relatively crude mixtures of FSH, LH and other contaminating proteins referred to herein as starting material sample(s) or starting material(s). The examples described in detail below use starting material samples obtained during pituitary hormone purification from pituitary glands or, alternatively, the sample is hMG prepared from human menopausal urine (natural FSH). Natural FSH "may also" be derived, for example, from immortalized human gonadotrope cell lines or tumors of gonadotrope cells. In any case, the sample is substantially free of TSH, prolactin and growth hormone and the FSH comprises about 2–5% of the sample. The LH contamination varies according to the sample but may be as high as 200%. Alternative sources of starting material include crude preparations of recombinantly produced FSH (recombinant FSH), including, for example, engineered molecules that retain FSH biological activity (Szkudlinski, et. al., 1996; U.S. Pat. No. 5,338,855). The sample can be prepared for DAC by standard methods of sample preparation including concentration-diafiltration or concentration and desalting using size exclusion chromatography. The sample is preferably equilibrated with sodium acetate with or without leupeptin as a protease inhibitor. More preferably, the sample is equilibrated with about 1 mM to about 5 mM sodium acetate containing about 1 $\mu$M to about 2 $\mu$M leupeptin at pH 4.0 to 5.5. Most preferably, the sample is equilibrated with 5 mM sodium acetate at pH 4.0. For longer term storage of these samples, it is preferable to use 1 mM to 5 mM Tris-acetate, more preferably 1 mM, as the equilibration buffer and maintain the sample pH at 7 to 9.5, more preferably pH 9.5. The sample may be stored liquid or frozen in this buffer without appreciable loss of FSH activity. The sample should only be exposed to low pH (e.g., about 4) for relatively short time periods just prior to its application to the DAC column. Longer-term exposure to 5 mM sodium acetate at pH 4.0 can lead to FSH inactivation.

The DAC column is prepared in a glass chromatography column of appropriate dimensions for the sample to be used and the target loading of the DAC media. The column is packed with the solid matrix comprising an appropriate dye coupled to the solid phase, preferably Mimetic Orange 1, manufactured by Affinity Chromatography Limited (US Distributor: Prometic BioSciences, Inc; Catalog number A6XL 0030). The column is then equilibrated with several column volumes, preferably at least 8, of sodium acetate at acidic pH at a flow rate of 60–120 cm/hr. The conductivity of the sample is desirably less than 1 mS prior to binding. The final sample is at acidic pH, preferably about 4.0, in either sodium acetate (preferably about 5 mM) or Tris-acetate (preferably about 1 mM). An aliquot of the sample final is taken for later assay. The sample is applied to the column, preferably at 30 cm/hr or less. Sample application is followed by elution with sodium acetate, at pH 4.0, for several column volumes at about 60 cm/hr. This is followed by washout of non-adsorbed LH and other proteins using $NaH_2PO_4$ at pH about 6.0. Elution with this buffer continues for a total of several column volumes at about 60 cm/hr. FSH is then eluted or released by running a several column volume linear gradient of NaCl, which also contains $NaH_2PO_4$ at pH about 6.0.

The following examples are intended to be descriptive of the instant invention and are in no way intended to limit the scope of the invention claimed herein.

EXAMPLE 1

Purification of FSH from Human Pituitary Glands

The sample used for FSH purification was derived from a process used for the extraction and purification of LH, FSH, and TSH. The method was adapted from the method of Hartree (1966). The side fraction used for FSH purification was derived from an acid extract (pH 4.0) of 3218 glands that was initially processed through cation exchange chromatography (CIX) on Fractogel EMD $SO_3$-650M (EM Separations Technology, Gibbstown, N.J.). The extract was bound to this resin at pH 4.5 in 0.1 M NaCl, 10 mM sodium acetate. The hormones were eluted by use of a 10 column-volume linear gradient to 0.8 M NaCl, 8 mM sodium acetate, pH 4.5. This step resulted in nearly quantitative recoveries of LH, FSH and TSH and 5- to 10-fold purification of the hormones. The sample containing TSH, LH and FSH resulting from CIX was concentrated 10-fold and brought to 1.5M ammonium sulfate by the addition of solid ammonium sulfate. It was then bound to PAE 1000 L (Amicon, Inc.) using a batch procedure. Following washout with 1.5M ammonium sulfate, 20 mM sodium acetate, pH 4.5, TSH was separated from LH and FSH by elution with a 15 column-volume reverse salt gradient to 0.25M ammonium sulfate, 20 mM sodium acetate, pH 4.5, followed by a step to 20 mM sodium acetate, pH 4.5.

The sample prepared as set forth above contained 852,480 IUs FSH, 1,868,130 IUs LH, and 3800 mgs of total protein. The hormones were determined by immunoassay using either the Abbott ImX or Chiron Diagnostics ACS-180 method. Total protein was determined using the absorbance at 280 nm, using a cuvette with a 1 cm path length and assuming that a solution of 1 mg/ml total protein yields 1.00 absorbance units. The initial sample was in a buffer containing 1.25 M ammonium sulfate, 20 mM Tris, 1 $\mu$M leupeptin at pH 8.6. This was prepared for chromatography on Orange 1 by concentration from 10.325 Lt. to about 600 mls in a hollow fiber ultrafiltration device (M12, ProFlux™, Amicon, Inc) equipped with a 10,000 Dalton-cutoff membrane (S10Y10, Amicon, Inc.). Concentration occurred at a flow rate of 3 Lt./min with 15 PSI back pressure applied to the hollow fiber cartridge. The sample was then diafiltered with 1 mM Tris-acetate, 1 $\mu$M leupeptin at pH 9.5 until the conductivity of the sample was less than 1 mS. The sample was recovered from the M12 and the hollow fiber cartridge was washed out with 2×300 mls of 1 mM Tris-acetate, 1 $\mu$M leupeptin at pH 9.5. These washes were combined with the concentrated sample to form the sample final. It was then centrifuged at 6500 RPM for 15 minutes and the volume of the supernatant was measured. The conductivity and A280 were determined and a small aliquot was removed for immunoassay. The sample final may be stored at 4° C. or –20° C. In this example, its pH was adjusted to 4.0 with acetic acid following preparation of the column as described below. The sample final is adjusted to pH 4.0 just prior to its application to the chromatography column.

The chromatography column was glass, 4.4x25 cm (Vantage L, VL 44x250, Amicon, Inc.). It was packed and operated at room temperature. The column was packed with Mimetic Orange 1 (Prometic BioSciences, Inc; Catalog number A6XL 0030) according to the manufacturer's recommendations to a bed volume of 243 mls. The column was operated on a dual pump bio-chromatography system equipped with a computer controlled gradient formation system (Two pumps No.222C with 0–30 mL/min heads; controller model 232D; Scientific Systems, Inc.). It was equilibrated with start buffer (5 mM sodium acetate, 1 $\mu$M leupeptin, pH 4.0) at 60 cm/hr. Prior to sample application to the column, the eluate pH was 3.8 to 4.3 and its conductivity was <1.3 mS.

The sample final, which had been previously adjusted to pH 4.0 with acetic acid, was then applied to the column at 15 cm/hr. A peristaltic pump was used for sample application. The column was loaded at 15 mg/mL total protein to packed bed volume. The column was then eluted according to a programmed elution regime. The flow rate was 60 cm/hr throughout elution: 10 column volumes with start buffer (5 mM sodium acetate, 1 µM leupeptin, pH 4.0); 10 column volumes with washout buffer (0.025 M NaH$_2$PO$_4$, 0.02% NaN$_3$, 1 µM leupeptin, pH 6.0); 10 column volume linear gradient from washout buffer to elution buffer (0.025 M NaH$_2$PO$_4$, 2.0 M NaCl, 1 µM leupeptin, 0.02% NaN$_3$, pH 6.0). Elution with washout buffer is effective in removing unbound LH and other contaminating proteins as well. The column eluate is collected by a fraction collector and the fractions are analyzed to determine total protein, FSH and LH immunological activity. The column is stored in 0.1 M NaCl/EtOH (75/25) (v/v). FSH is recovered from the DAC process at relatively high purity (see Table 1). The LH contamination was reduced from 78.3% to 1.3%.

Hydrophobic interaction chromatography may be used to remove residual amounts of LH from FSH. The FSH-containing fractions from the DAC run are eluted during the gradient to elution buffer as a rather broad peak following an earlier, sharper peak containing LH and non-hormone contaminates. This FSH sample is prepared for HIC by first pooling the FSH-containing fractions from the DAC run and then adjusting the sample pH to 8.5 with NaOH. The sample is then concentrated to 1–2 mgs/mL FSH using a hollow fiber ultrafiltration device equipped with a 10,000 Dalton cutoff membrane (AG Technologies, Cat. No.UFP-10-E-4A). The sample is diafiltered with 5 to 10 volumes of 1 mM Tris-acetate at pH 8.5. This sample may be stored at 4° C. or −20° C.

The chromatography column is glass, 1.6x20 cm (Pharmacia XK16x20). It is packed and operated at room temperature. The column is packed with Bakerbond™ Wide Pore HI-Propyl, Cat. No.7182-02 according to the manufacturer's recommendations to a bed volume of 12 mls. The column is operated on a dual pump bio-chromatography system equipped with a computer controlled gradient formation system (two pumps No.222C with 0–30 mL/min heads; controller model 232D; Scientific Systems, Inc.). It is equilibrated with start buffer (1.5M ammonium sulfate, 20 mM sodium acetate, 1 µM leupeptin, pH 4.5) at 150 cm/hr. Prior to sample application to the column, the eluate pH is 4.3 to 4.7 and its conductivity is equal to that of the start buffer.

The sample final is adjusted to pH 4.5 with acetic acid and brought to 1.5 M ammonium sulfate by addition of solid ammonium sulfate. A peristaltic pump is used for sample application. The column is loaded at 10 mg/mL total protein. The column was then eluted according to a programmed elution regime. The flow rate was 150 cm/hr throughout elution: linear gradient to 60% elution buffer (20 mM sodium acetate, 1 µM leupeptin, pH 4.5) in 30 column volumes; hold for 10 column volumes; linear gradient from 60% to 100% elution buffer in 2 column volumes. The eluate is collected by a fraction collector and the total protein and FSH immunological activity of these fractions is determined. FSH-containing fractions from HIC were pooled to form the final product which was then concentrated to about 7600 IUs/mL and diafiltered with 50 mM ammonium bicarbonate. Diafiltration occurred in a stirred cell device (Model 8400, Amicon, Inc.) equipped with a 10,000 Dalton ultrafiltration membrane (YM-10, Amicon, Inc.).

Table 1 shows the data obtained from the DAC and HIC procedures used to produce a lot of affinity pure human FSH. The final product contained 0.39 IUs LH/mg of FSH or 0.0038% and 0.0046 IUs TSH/mg FSH or 0.054%. Analysis of the product by SDS-PAGE using the reducing system of Laemmlli (1970) stained with Coomassie Blue for protein revealed a single broad band at 21,000 to 23,000 Daltons. No other protein bands were detected. The single band is likely to contain both the alpha and beta subunits of FSH as these are known to co-migrate in this system. (Keene, J. L., et. al., 1989). The alpha and beta subunits of FSH can be resolved by use of isoelectric focusing.

Several lots have been produced using these same procedures with substantially similar results. Similar procedures also have been applied to bovine pituitary glands, which resulted in approximately 35-fold purification of bovine FSH by DAC using Orange 1 as described herein.

TABLE 1

FSH Purification from human pituitary glands.

| SAMPLE | IUs FSH | IUs LH | Protein (Mgs) | FSH Imm. Act (IUs/Mg) | Purification | % Yield |
|---|---|---|---|---|---|---|
| Pituitary Extract | 853,477 | 2,160,000 | 160,115 | 5.33 | N.A. | 100 |
| DAC SF | 852,480 | 1,868,130 | 3800 | 224.6 | 42.1 | 99.9 |
| DAC Product | 837,670 | 29,960 | 78.6 | 10,657 | 47.5 | 98.3 |
| HIC SF | 641,162 | N.D. | 79 | 8116 | 0.76 | 76.5 |
| HIC Product | 431,170 | 30 | 46.6 | 9253 | 1.14 | 67.0 |
| Final Product | 318,697 | 26.5 | 45.1 | 7066 | 0.76 | 73.9 |
| Overall | | | | | | 37.3 |

EXAMPLE 2

Purification of FSH from Human Menopausal Gonadotropin

A sample of hMG was commercially obtained (Y.J. Bioproducts, Rancho Cordova, Calif.). It was provided at a potency of 177 IU/mg as determined by EIA and RIA. This sample was prepared for DAC on Orange 1 by reconstitution at 7.5 mg/mL in 1 mM Tris-acetate, 1 mM leupeptin, pH 9.5. To prepare the sample for binding to Orange 1, it was diafiltered with 5 to 10 volumes of the same buffer as used for reconstitution. Diafiltration occurred in a stirred cell device (Model 8400, Amicon, Inc.) equipped with a 10,000 Dalton ultrafiltration membrane (YM-10, Amicon, Inc.). The sample final conductivity was 0.65 mS and the total protein was 5.26 mg/mL. An aliquot of this sample was taken for FSH and LH determination by immunoassay.

Chromatography was done in a glass column 1.6x20 cm (Amicon, Inc.) which was packed with Mimetic Orange 1 manufactured by Affinity Chromatography Limited (US Distributor: Prometic BioSciences, Inc; Catalog number A6XL 0030) to a bed volume of 11 mls. The column was equilibrated with start buffer (5 mM sodium acetate, 1 µM leupeptin, pH 4.0) at 3 mls/min for at least 8 column volumes. Prior to sample application to this column, the eluate pH was 3.8–4.3 and its conductivity was <1.3 mS. Chromatography occurred on a single pump bio-chromatography system equipped with a proportioning value allowing ternary gradient formation (Scientific Systems, Inc. Series III Digital Pump).

The sample final was adjusted to pH 4.0 with acetic acid and was then applied to the column at 15 cm/hr. The sample was applied to the column using a 50 mL superloop (Pharmacia, Inc.) and a Reodyne injection valve (Model 9125). The column was loaded at 14.4 mg/mL total protein. The column was then eluted according to a programmed elution regime. All elution was performed at 60 cm/hr: 10 column volumes with start buffer (5 mM sodium acetate, 1 µM leupeptin, pH 4.0); 10 column volumes with washout buffer (0.025 M NaH$_2$PO$_4$, 0.02% NaN$_3$, 1 μM leupeptin, pH 6.0); 10 column volume linear gradient from washout buffer to elution buffer (0.025 M NaH$_2$PO$_4$, 2.0 M NaCl, 1 μM leupeptin, 0.02% NaN$_3$, pH 6.0). The column eluate is collected by a fraction collector and the fractions are analyzed to determine total protein FSH and LH immunological activity, as described in Example 1. The column is stored in 0.1M NaCl/EtOH (75/25) (v/v).

In this example, the LH contamination in the FSH product of the DAC procedure was 3.45 IUs/mg FSH or 0.03%. However, the FSH product specific activity was 3250 IUs/mg and, by SDS-PAGE analysis, the FSH was estimated to be 95% pure. There was another band at about 27,000 Daltons in addition to the prominent FSH band at 22,000 to 24,000 Daltons. Hence, the FSH from the DAC procedure was further purified by HIC.

The FSH-containing fractions from the DAC run are eluted during the gradient to elution buffer as a rather broad peak following an earlier, sharper peak containing LH and non-hormone contaminants. This elution profile is nearly identical to that seen with DAC of human pituitary-derived FSH. The FSH sample is prepared for HIC by first pooling the FSH-containing fractions from the DAC run. The sample is then concentrated to 3800–7600 IUs/mL FSH using a stirred cell ultrafiltration device (Model 8400, Amicon, Inc.) equipped with a 10,000 Dalton cutoff membrane (YM-10, Amicon, Inc.) The sample was diafiltered with 5 to 10 volumes of 50 mM ammonium bicarbonate at pH 8.1.

The chromatography column was glass, 5x50 mm (Pharmacia HR5/50). It was packed and operated at room temperature. The column was packed with Bakerbond™ Wide Pore HI-Propyl, Cat. No.7182-02 according to the manufacturer's recommendations to a bed volume of 1.2 mls. The column was operated on a completely automated bio-chromatography system (Akta Explorer, Pharmacia, Inc.). It was equilibrated with start buffer (1.2 M ammonium sulfate, 20 mM sodium acetate, 1 μM leupeptin, pH 4.5) at 150 cm/hr. Prior to sample application to the column, the eluate pH is 4.3 to 4.7 and its conductivity is equal to that of the start buffer.

The sample final is adjusted to pH 4.5 with acetic acid and brought to 1.2 M ammonium sulfate by addition of solid ammonium sulfate and then injected onto the column. The column is loaded at 0.5 mg/mL total protein. The column is then eluted according to a programmed elution regime. All elutions are performed at 150 cm/hr: linear gradient to 70% elution buffer (20 mM sodium acetate, 1 μM leupeptin, pH 4.5) in 30 column volumes; hold for 10 column volumes; liner gradient from 70% to 100% elution buffer in 2 column volumes. The eluate is collected by a fraction collector and the total protein and FSH immunological activity of these fractions is determined as described previously.

Table 2 shows the data obtained from the DAC and HIC procedures used to produce a lot of affinity pure human urofollitropin or urinary-derived FSH (uFSH). The final product contained 1.6 IUs LH/mg of FSH or 0.015%; 0.001 IUs TSH/mg FSH or 0.017% and 0.2 IUs hCG/Mg or 0.0015%. Analysis of the product by SDS-PAGE using the reducing system of Laemmlli (1970) stained with Coomassie Blue for protein revealed a single broad band at 22,000 to 24,000 Daltons. No other protein bands were detected. The single band is likely to contain both the alpha and beta subunits of FSH as these are known to co-migrate in this system (Keene, J. L., et al., 1989). The alpha and beta subunits of FSH can be resolved by use of isoelectric focusing.

The biological activity of the final product was 8287 IUs/mg using an assay comprising an in vitro cell line containing recombinant human FSH receptor and a cAMP responsive luciferase reporter gene (Albanese, et al., 1994). The ratio of biological to immunological activity was 1.32; this parameter ranged from 1.3 to 1.7 in different preparations." Similar results were obtained by identical processing of other samples of hMG at 100 to 200 IUs/Mg FSH activity.

TABLE 2

FSH Purification from human menopausal gonadotropin.

| SAMPLE | IUs FSH | IUs LH | Protein (Mgs) | FSH Imm. Activity (IUs/Mg) | Purification | % Yield |
|---|---|---|---|---|---|---|
| DAC SF | 22,346 | 285 | 126 | 177 | NA | 100 |
| DAC Product | 20,151 | 18.5 | 5.46 | 3691 | 20.9 | 90.2 |
| HIC SF | 21,099 | ND | 4.897 | 4309 | 1.17 | 104.7 |
| HIC Product | 10,805 | ND | 1.91 | 5657 | 1.31 | 51.2 |
| Final Product | 9005 | 3.68 | 1.43 | 6298 | 1.11 | 83.3 |
| Overall | | | | | | 40.3 |

Less pure hMG may also be purified using the DAC and HIC procedures outlined above. However, hMG at 10 to 30 IU/mg also requires purification by ion exchange chromatography. An hMG sample of 15 IU/mg FSH was first subjected to DAC, according to the method described above, followed by CIX on Fractogel EMD SO$_3$-650M (EM Separations Technology, Gibbstown, N.J.) according to the procedure used to purify human FSH from pituitary extracts (Example 1). The resulting FSH was then purified to homogeneity by HIC, as described in Example 4.

EXAMPLE 3

Optimization of Dye Affinity Chromatography of FSH

The DAC procedure was subjected to a variety of experimental conditions in order to determine the optimum conditions for human FSH purification. These studies were performed on a scaled-down version of the above-described chromatography systems used for purification of FSH from human pituitary glands or from hMG. Initial studies showed the importance of binding at low pH and low conductivity for the separation of pituitary LH and FSH. When binding to Orange 1 occurred at pH 6.0 (25 mM NaH$_2$PO$_4$), both LH and FSH bound tightly and separation of LH and FSH during elution was incomplete. It was further shown that LH loading was maximal at 8,000 IUs/mL (0.76 mgs LH/mL) Orange 1. Above this loading, LH spilled over into the non-adsorbed fractions. FSH loading is maximal at approximately 0.25 mg FSH/mL.

Studies using hMG as a sample also confirmed the importance of binding conditions for the separation of gonadotropins by DAC on Orange 1. As the binding pH was varied from pH 4.0, 5.0 and 5.5 in 5 mM sodium acetate, the FSH binding was 99.2%, 99.4% and 99.3% (Calculated from the amount applied minus the FSH recovered in the non-adsorbed fractions). However, the amount of hCG that bound to the column increased with the pH. Hence, optimum separation of hCG from FSH required use of pH 4.0 for binding, e.g., 5 mM sodium acetate at pH 4.0. Some hMG samples were found to be contaminated with hCG at about 2%. The origin of this hCG contamination is unknown.

Hence, for optimum separation of gonadotropins from human FSH derived from pituitary glands or postmenopausal urine, binding to Orange 1 in a low conductivity (0.5 to 1.0 mS) buffer at pH 4.0 is preferred.

Washout from Orange 1 is important for the removal of contaminates from the bound FSH and the purification achieved by the DAC procedure. A sample of hMG was used for experiments designed to determine optimum washout conditions. The effect of washout pH was first determined by using washout buffers of pH 6, 7, 8 (25 mM $NaH_2PO_4$) and pH 9 (25 mM Glycine). There was an increase in the amount of FSH recovered in the washout fractions as the pH of the washout buffer was increased. At pH 6, 1.9% of the applied FSH was recovered in the washout; at pH 7, 9.9% of the FSH was recovered in the washout; at pH 8, 11.6% of the applied FSH was recovered in the washout and at pH 9, 43.1% of the applied FSH was recovered in the washout. Hence, to optimize recovery and purification of FSH in DAC using Orange 1, the preferred washout buffer is at pH 6.0.

The effect of salt content on washout was also investigated. Phosphate buffer concentrations above 50 mM result in substantial washout of FSH together with contaminating proteins, e.g., 120 mM spills 30% of the bound FSH. While 50 mM phosphate buffer at pH 6 can be used as a washout buffer, this results in spill over of approximately 8% of the applied FSH. Hence, the preferred washout buffer for the purification of FSH is 25 mM phosphate buffer at pH 6.0.

Parameters affecting the elution of FSH were also investigated using an hMG sample. While elution from Orange 1 does occur with pH increases above pH 8, we have focussed on the use of sodium chloride gradients at pH 6 for the ease of use of these procedures in a production environment. A study of the effects of changing the gradient endpoint from 2M to 1M to 0.8M to 0.6M NaCl showed that a 10 column-volume gradient to 0.6 M NaCl was sufficient to completely elute the FSH bound to Orange 1.

Loading of Orange 1 was found to be dependent on the specific activity of the hMG sample. For hMG at 150–200 IU/mg, optimum sample load is 5 to 10 mgs/mL total protein to packed volume of Orange 1 while hMG samples at 10 to 30 IU/mg are applied at 40–50 mg/mL loading.

After 10 use cycles the Orange 1 is regenerated as follows. Elute the column with 3 volumes of deionized water, 4 volumes 0.5N NaOH, 4 volumes 5 mM EDTA-$Na_2$, 4 volumes of 5.0 M urea, 4 volumes of deionized water. The column is stored in 0.1M NaCl/EtOH (75/25) (v/v).

In summary, the preferred method for DAC of hMG is as follows:
1. Sample buffer is 1 mM Tris, pH 7.0. Reconstitute the sample in this buffer and diafilter with 3 to 5 volumes across a 10,000 Dalton cutoff ultrafiltration membrane. Sample pH is adjusted to 4.0 using acetic acid just prior to chromatography.
2. A column is packed with Orange 1 manufactured by Affinity Chromatography Limited (US Distributor: Prometic BioSciences, Inc; Catalog number A6XL 0030) in a suitable high performance glass chromatography column. Use packing material of use cycle <N.10, where N is the number of regenerations. The column is equilibrated with 8 to 10 volumes of start buffer (5 mM sodium acetate, pH 4.0).
3. The sample is applied to the column at 30 cm/hr to result in a loading of 5 to 50 mgs/mL, depending on the specific activity of the sample.
4. Washout the columns with 5 to 10 column volumes of start buffer at 60 cm/hr.
5. Washout the column with 10 to 15 column volumes of 25 mM $NaH_2PO_4$, pH 6.0 at 60 cm/hr.
6. Run a linear gradient from washout buffer to elution buffer (0.6M NaCl, 25 mM $NaH_2PO_4$, pH 6.0) at 60 cm/hr in 10 column volumes.
7. The column is stored in 0.1M NaCl/EtOH (75/25) (v/v).

EXAMPLE 4

Optimization of the Hydrophobic Interaction Chromatography of Urofollitropin

As is shown in Table 2, the yield of FSH from the HIC procedure was 51% and the purification was 1.3-fold. While the product of this HIC procedure was homogeneous by SDS-PAGE and its contamination with LH was minimal, optimization was undertaken to improve the yield of this procedure. These studies were performed on a scaled-down version of the above-described chromatography systems used for purification of FSH from hMG. It was found that addition of an organic solvent to the elution buffer improved the yield of FSH from HIC on a C3 solid phase (Source 15 Iso, Pharmacia, Inc.). The yield of urofollitropin was 77.9% using a reverse salt gradient from 1.5 M $K_2HPO_4$, pH 8.5 to 20 mM Tris, pH 8.5. When the elution buffer contained 30% ethanol, the yield was quantitative.

A media screen experiment using resins of differing hydrophobicity investigated various alkyl substituents, including propyl, butyl, hexyl, octyl and decyl groups immobilized to cross-linked agarose (Prometic BioSciences, Inc.). In these runs, the start buffer was 1.5M K2HPO4, pH 8.5, and the elution buffer was 20 mM $Na_2HPO_4$, 30% ethanol, pH 8.5. Each column was equilibrated with 5 column volumes start buffer and, following sample injection, the column was washed out with 10 volumes of start buffer. Elution occurred by running a 20-column volume, linear gradient to elution buffer. The flow rate was 120 cm/hr throughout the run. The results showed quantitative recoveries of FSH from all five of the HIC resins. However, the greatest clearance of residual hCG from FSH occurred with the decyl resin. Hence, the preferred method for the HIC of urofollitropin uses decyl-agarose 6XL resin (Prometic BioSciences, Inc.). The method was further optimized by using a flow rate of 90 cm/hr during sample application and washout. FSH was eluted at 60 cm/hr using a 10 column volume linear gradient from start to elution buffer. This is the preferred method for HIC of human FSH.

While the exemplary preferred embodiments of the present invention are described herein with particularity, those having ordinary skill in the art will recognize various changes, modifications, additions, and applications other than those specifically described herein, and may adapt the preferred embodiments and methods without departing from the spirit of the invention.

All documents cited herein are incorporated herein by reference.
Documents cited:
1. Albonese, C., Christin-Maitre, S., Sluss, P. M., Crowley, W. F., and Jameson, J. L., Development of a bioassay for FSH using a recombinant human FSH receptor and a cAMP responsive luciferase reporter gene. Molec. Cell. Endocrin. 101: 211–219, 1994.
2. Bonde, M., Frokier, H., and Pepper, D. S., Selection of monoclonal antibodies for immunoaffinity chromatography: model studies with antibodies against soy bean trypsin inhibitor. J. Biochem. Biophys. Meth. 23: 73–82, 1991.

3. Chappel, S. C., Ulloa-Aguirre, A., and Coutifaris, C., Biosynthesis and secretion of follicle-stimulating hormone. Endoc. Revs. 4:179–211, 1983.
4. Donini, P., Puzzuoli, D., D'Alessio, I., Lunenfeld, B., Eshkol, A. and Parlow, A. F., Purification and separation of follicle stimulating hormone (FSH) and luteinizing hormone (LH) from human postmenopausal gonadotropin (HMG). II. Preparation of biological apparently pure FSH by selective binding of LH with an anti-HCG serum and subsequent chromatography. Acta Endocrinol. 52: 186–198, 1966.
5. Garg, N., Galaev, I. Y., and Mattiasson, B., Dye-affinity techniques for bioprocessing: recent developments. J. Mol. Recognit. 9: 259–274, 1996.
6. Hartree, A. S., Separation and partial purification of protein hormones from human pituitary glands. Biochem. J. 100: 754–761, 1966.
7. Hoffman, W. L. and O'Shannessy, D. J., Site-specific immobilisation of antibodies by their oligosaccharide moieties to new hydrazide derivatised solid supports. J. Immunol. Methods 112: 113–120, 1988.
8. Jack, G. W., Blazek, R., James, K., Boyd, J. E., and Micklem, L. R., The automated production by immunoaffinity chromatography of the human pituitary glycoprotein hormones thyrotropin, follitropin and lutropin. J.Chem. Tech. Biotechnol. 39: 45–58,1987.
9. Jack, G. W., Immunoaffinity chromatography. Molec. Biotech. 1:59–86, 1994.
10. Keene, J. L., Matzuk, M. M., Otani, T., Fauser, B. C. J. M., Galway, A. B., Hsueh, A. J. W., and Boime, I., Expression of biologically active human follitropin in Chinese hamster ovary cells. J. Biol. Chem. 264:4769–4775, 1989.
11. Knight, P. G. Roles of inhibins, activins, and follistatin in the female reproductive system. Front.Neuroendocrinol. 17: 476–509, 1996.
12. Lowe, C. R., Burton, S. J., Burton, N. P., Alderton, W. K., Pitts, J. M. and Thomas, J. A., Designer dyes: 'biomimetic' ligands for the purification of pharmaceutical proteins by affinity chromatography. Trends in Biotech. 10: 442–448, 1992.
13. Moore, L. G., Ng-Chie, W., Lun, S.,Lawrence, S. B., Young, W., McNatty, K. P., Follicle-stimulating hormone in the brushtail possum (Trichosurus vulpecula): purification, characterization and radioimmunassay. Gen. Comp. Endocrinol. 106:30–38, 1997.
14. Roos, P., Human Follicle-stimulating hormone. Acta Endocrinol. Suppl. 131, 9–93, 1968.
15. U. K. Laemmli, Cleavage of structural proteins during the assembly of the head of bacteriophage T4. Nature 227:680–685, 1970.
16. Szkudlinski, M. W., Teh, N. G., Grossman, M., Tropea, J. E., and Weintraub, B. D., Engineering human glycoprotein hormone superactive analogs. Nature Biotech. 14: 1257"–1263, 1996".
17. Japanese patent number 8,027,181. Purification of sialic acid-containing glycoprotein, used in foods, cosmetic, pharmaceuticals, etc.-comprises using chitosan porous beads.
18. Great Britain patent number 8,510,177. Isolating biologically active pituitary glycoprotein hormones by affinity chromatography, eluting with acidic buffer free of protein denaturant.
19. U.S. Pat. No. 5,128,453. Urinary follicle-stimulating hormone.
20. U.S. Pat. No. 5,338,835. Extended follicle stimulating subunit-has carboxy terminal peptide with residues of human chorionic gonadotropin beta subunit.

What is claimed is:

1. A method for purification of FSH from a sample comprising the steps of:
    (a) applying the sample in a buffer of a pH of less than about 6.0 to a dye affinity chromatography matrix comprising a solid matrix having a dye ligand;
    (b) washing out contaminants from the solid matrix with a buffer of less than 50 mM salt and of a pH of less than about 9.0;
    (c) and eluting the FSH in a salt buffer wherein the FSH is released from the solid matrix at a salt concentration of less than about 0.8 M NaCl, wherein the FSH is human urinary FSH, human recombinant FSH, human FSH secreted from gonadotropes maintained in in-vitro cell culture, bovine FSH, equine FSH, porcine FSH, ovine FSH, canine FSH, rat FSH, feline FSH or monkey FSH.

2. The method of claim 1 wherein the dye ligand is Orange 1 or Orange 2.

3. The method of claim 1 wherein the dye ligand is yellow 2 or green 1.

4. The method of claim 1 wherein the solid matrix further comprises cross-linked agarose triazine coupled to Orange 1.

5. The method of claim 1 wherein the contaminants are washed out from the solid matrix with a buffer of less than 50 mM phosphate.

6. The method of claim 1 further comprising the step of purifying the FSH by chromatography on a hydrophobic solid phase.

7. The method of claim 6 wherein the hydrophobic solid phase comprises a propyl, butyl, hexyl, octyl or decyl alkyl group.

8. The method of claim 1 wherein the sample is applied in a buffer of less than 1 mS conductivity and a pH of about 4.0.

9. The method of claim 1, wherein the solid matrix further comprises cross-linked agarose triazine coupled to Orange 1; the sample is applied in a buffer of less than 1 mS conductivity and a pH of about 4.0; the contaminants are washed out from the solid matrix with a buffer of less than 50 mM phosphate; and the FSH is eluted by a salt gradient of from about 0.0 M NaCl to about 0.6 M NaCl at a pH of about 6.0.

10. The method of claim 9 further comprising the step of purifying the FSH by chromatography on a hydrophobic solid phase.

11. The method of claim 10 wherein the hydrophobic solid phase comprises a propyl, butyl, hexyl, octyl or decyl alkyl group.

12. The method of claim 1 wherein the FSH is human urinary FSH.

13. The method of claim 1 wherein the FSH is human recombinant FSH.

14. The method of claim 1 wherein the FSH is human FSH secreted from gonadotropes maintained in in-vitro cell culture.

15. A method for purification of FSH from a sample comprising the steps of:
    (a) applying the sample in a buffer of a pH of less than about 6.0 to a dye affinity chromatography matrix comprising a solid matrix having a dye ligand;
    (b) washing out contaminants from the solid matrix with a buffer of less than 50 mM salt and of a pH of less than about 9.0;

(c) and eluting the FSH with a buffer of a pH of greater than or equal to about 8.0, wherein the FSH is human urinary FSH, human recombinant FSH, human FSH secreted from gonadotropes maintained in in-vitro cell culture, bovine FSH, equine FSH, porcine FSH, ovine FSH, canine FSH, rat FSH, feline FSH or monkey FSH.

16. A method for purification of FSH from a sample comprising the steps of:

(a) applying the sample in a buffer of a pH of less than about 6.0 to a dye affinity chromatography matrix comprising a solid matrix having a dye ligand;

(b) washing out contaminants from the solid matrix with a buffer of less than 50 mM salt and of a pH of less than about 9.0;

(c) and eluting the FSH with a buffer comprising a competitor of FSH binding to the dye ligand, wherein the FSH is human urinary FSH, human recombinant FSH, human FSH secreted from gonadotropes maintained in in-vitro cell culture, bovine FSH, equine FSH, porcine FSH, ovine FSH, canine FSH, rat FSH, feline FSH or monkey FSH.

* * * * *